United States Patent
Hietala et al.

(10) Patent No.: US 12,145,906 B2
(45) Date of Patent: Nov. 19, 2024

(54) RENEWABLE CHEMICAL PRODUCTION ENGAGING METATHESIS AND MICROBIAL OXIDATION

(71) Applicant: Neste Oyj, Espoo (FI)

(72) Inventors: Jukka Hietala, Porvoo (FI); Jukka Räsänen, Porvoo (FI); Anja Leminen, Porvoo (FI); Virpi Rämö, Porvoo (FI)

(73) Assignee: NESTE OYJ, Espoo (FI)

(*) Notice: Subject to any disclaimer, the term of this patent is extended or adjusted under 35 U.S.C. 154(b) by 0 days.

(21) Appl. No.: 17/762,974

(22) PCT Filed: Sep. 25, 2020

(86) PCT No.: PCT/FI2020/050632
§ 371 (c)(1),
(2) Date: Mar. 23, 2022

(87) PCT Pub. No.: WO2021/058877
PCT Pub. Date: Apr. 1, 2021

(65) Prior Publication Data
US 2022/0356131 A1 Nov. 10, 2022
US 2023/0339828 A2 Oct. 26, 2023

(30) Foreign Application Priority Data
Sep. 26, 2019 (FI) .................................... 20195822

(51) Int. Cl.
| | | |
|---|---|---|
| C07C 6/04 | (2006.01) | |
| C07C 1/22 | (2006.01) | |
| C07C 5/22 | (2006.01) | |
| C07C 51/36 | (2006.01) | |
| C07C 51/44 | (2006.01) | |
| C07C 67/333 | (2006.01) | |
| C10G 3/00 | (2006.01) | |
| C10M 101/04 | (2006.01) | |
| C10M 177/00 | (2006.01) | |
| C10N 70/00 | (2006.01) | |
| C12P 7/6409 | (2022.01) | |

(52) U.S. Cl.
CPC .................. *C07C 6/04* (2013.01); *C07C 1/22* (2013.01); *C07C 5/22* (2013.01); *C07C 51/36* (2013.01); *C07C 51/44* (2013.01); *C07C 67/333* (2013.01); *C10G 3/42* (2013.01); *C10M 101/04* (2013.01); *C10M 177/00* (2013.01); *C12P 7/6409* (2013.01); *C10G 2300/1011* (2013.01); *C10M 2203/1025* (2013.01); *C10N 2070/00* (2013.01)

(58) Field of Classification Search
CPC .... C07C 6/04; C07C 1/22; C07C 5/22; C07C 51/36; C07C 51/44; C07C 67/333; C10G 3/42; C10G 2300/1011; C10M 101/04; C10M 2203/1025
See application file for complete search history.

(56) References Cited

U.S. PATENT DOCUMENTS

| | | |
|---|---|---|
| 3,823,070 A | 7/1974 | Minato et al. |
| 3,912,586 A | 10/1975 | Kaneyuki et al. |
| 7,256,301 B2 | 8/2007 | Erguen et al. |
| 8,580,985 B2 | 11/2013 | Thompson et al. |
| 8,753,853 B2 | 6/2014 | Ritter et al. |
| 9,023,626 B2 | 5/2015 | Dubois |
| 9,676,884 B2 | 6/2017 | Rizvi et al. |
| 11,021,416 B2 | 6/2021 | Bosetti et al. |
| 11,459,280 B2 | 10/2022 | Bosetti et al. |
| 2004/0082042 A1 | 4/2004 | Staley |
| 2005/0284940 A1 | 12/2005 | Enomoto et al. |
| 2006/0079704 A1 | 4/2006 | Lacombe et al. |
| 2007/0131579 A1 | 6/2007 | Koivusalmi et al. |
| 2007/0135663 A1 | 6/2007 | Aalto et al. |
| 2010/0191008 A1 | 7/2010 | Olson |
| 2010/0305354 A1 | 12/2010 | Dubois |
| 2011/0113679 A1 | 5/2011 | Cohen et al. |
| 2011/0300594 A1 | 12/2011 | Ritter et al. |
| 2012/0197032 A1 | 8/2012 | Firth et al. |
| 2012/0253069 A1 | 10/2012 | Zang et al. |
| 2013/0217906 A1 | 8/2013 | Kunz et al. |
| 2013/0225409 A1 | 8/2013 | Allen et al. |
| 2013/0225473 A1 | 8/2013 | Allen et al. |
| 2014/0005423 A1 | 1/2014 | Allen et al. |
| 2014/0031592 A1 | 1/2014 | Shinde |
| 2014/0228586 A1 | 8/2014 | Beardslee et al. |
| 2014/0275595 A1 | 9/2014 | Wampler et al. |
| 2015/0087521 A1 | 3/2015 | Allen et al. |

(Continued)

FOREIGN PATENT DOCUMENTS

| | | |
|---|---|---|
| CN | 101360810 A | 2/2009 |
| CN | 101868552 A | 10/2010 |

(Continued)

OTHER PUBLICATIONS

Office Action issued on May 11, 2022, by the Canadian Patent Office in corresponding Canadian Patent Application No. 3,149,520. (4 pages).

Ahmad, F. B. H., et al., "Co-Metathesis Reaction of Crude Palm Oil and Ethene", JAOCS, 1995, vol. 72, No. 6, pp. 757-758, AOCS Press. (2 pages).

Alm, M., "Animal Fats", 2013, AOCS Lipid Library [online]. Available at https://lipidlibrary.aocs.org/edible-oilprocessing/animal-fats [Accessed Aug. 27, 2019]. (21 pages).

(Continued)

*Primary Examiner* — Paul J Holland

(74) *Attorney, Agent, or Firm* — Buchanan Ingersoll & Rooney PC

(57) ABSTRACT

A process for combined renewable 1-decene and renewable carboxylic diacid production from a fatty acid ester containing feedstock, wherein the feedstock is first subjected to metathesis reaction conditions, recovery of 1-decene and then to microbial oxidation to yield diacids in a fermentation broth. Diacids of unusual carbon chains lengths are thereby obtainable.

23 Claims, 3 Drawing Sheets

(56) References Cited

U.S. PATENT DOCUMENTS

| | | |
|---|---|---|
| 2015/0210855 A1 | 7/2015 | Firth et al. |
| 2015/0353996 A1 | 12/2015 | Hoo et al. |
| 2015/0361024 A1 | 12/2015 | Laplaza |
| 2016/0251278 A1 | 9/2016 | Bosetti et al. |
| 2016/0298145 A1 | 10/2016 | Laplaza et al. |
| 2016/0340616 A1 | 11/2016 | Littich et al. |
| 2017/0137365 A1 | 5/2017 | Wampler et al. |
| 2019/0071611 A1 | 3/2019 | Goossen et al. |
| 2020/0181503 A1 | 6/2020 | Myllyoja et al. |
| 2020/0181504 A1 | 6/2020 | Myllyoja et al. |
| 2020/0181527 A1 | 6/2020 | Kulmala et al. |
| 2021/0171420 A1 | 6/2021 | Bosetti et al. |
| 2022/0009855 A1 | 1/2022 | Myllyoja et al. |
| 2022/0340835 A1 | 10/2022 | Myllyoja et al. |
| 2022/0363613 A1 | 11/2022 | Hietala et al. |

FOREIGN PATENT DOCUMENTS

| | | |
|---|---|---|
| CN | 102439118 A | 5/2012 |
| CN | 102498086 A | 6/2012 |
| CN | 102770520 A | 11/2012 |
| CN | 102781583 A | 11/2012 |
| CN | 104837802 A | 8/2015 |
| CN | 105189576 A | 12/2015 |
| CN | 106170530 A | 11/2016 |
| CN | 107001217 A | 8/2017 |
| EP | 1741768 A1 | 1/2007 |
| EP | 2155838 B1 | 9/2014 |
| ES | 2595106 T3 | 12/2016 |
| FI | 100248 B | 10/1997 |
| WO | 0017380 A1 | 3/2000 |
| WO | 0104337 A1 | 1/2001 |
| WO | 0121572 A1 | 3/2001 |
| WO | 2007068795 A1 | 6/2007 |
| WO | 2007068796 A2 | 6/2007 |
| WO | 2007068796 A3 | 8/2007 |
| WO | 2008046106 A2 | 4/2008 |
| WO | 2008048522 A1 | 4/2008 |
| WO | 2008140468 A2 | 11/2008 |
| WO | 2010068904 A2 | 6/2010 |
| WO | 2011046872 A2 | 4/2011 |
| WO | 2011056881 A2 | 5/2011 |
| WO | 2012061093 A1 | 5/2012 |
| WO | 2012129477 A1 | 9/2012 |
| WO | 2014058867 A1 | 4/2014 |
| WO | 2015108874 A1 | 7/2015 |
| WO | 2016014417 A1 | 1/2016 |
| WO | 2016062868 A1 | 4/2016 |
| WO | 2018234187 A1 | 12/2018 |

OTHER PUBLICATIONS

Bosma, R. H. A., et al., "Cometathesis of Methyl Oleate and Ethylene; a Direct Route to Methyl Dec-9-enoate", J. C. S. Chem. Comm., 1981, pp. 1132-1133. (2 pages).

Chikkali, S. et al., "Refining of Plant Oils to Chemicals by Olefin Metathesis", Angew. Chem. Int. Ed., 2012, vol. 51, pp. 5802-5808, Wiley Online Library, Wiley-VCH Verlag Gmbh & Co. KGaA, Weinheim, DE. (7 pages).

Communication of Acceptance under section 29a of Patents Decree issued in corresponding Finnish Patent Application No. 20195820 by the Finnish Patent and Registration Office dated Sep. 15, 2020. (3 pages).

Communication of Acceptance under section 29a of Patents Decree issued in corresponding Finnish Patent Application No. 20195822 by the Finnish Patent and Registration Office dated Sep. 15, 2020. (3 pages).

Communication of Acceptance under section 29a of Patents Decree issued in corresponding Finnish Patent Application No. 20195823 by the Finnish Patent and Registration Office dated Sep. 15, 2020. (3 pages).

Finnish Search Report for Finnish Patent Application No. 20195823 dated Jan. 23, 2020 (3 pages).

Finnish Search Report for Finnish Patent Application No. 20195820 dated Jan. 24, 2020 (4 pages).

Finnish Search Report for Finnish Patent Application No. 20195822 dated Jan. 24, 2020 (3 pages).

International Search Report (PCT/ISA/210) and Written Opinion (PCT/ISA/237) mailed on Nov. 20, 2020, by the European Patent Office as the International Searching Authority for International Application No. PCT/FI2020/050630. (16 pages).

International Search Report (PCT/ISA/210) and Written Opinion (PCT/ISA/237) mailed on Nov. 20, 2020, by the European Patent Office as the International Searching Authority for International Application No. PCT/FI2020/050631. (16 pages).

International Search Report (PCT/ISA/210) and Written Opinion (PCT/ISA/237) mailed on Dec. 16, 2020, by the European Patent Office as the International Searching Authority for International Application No. PCT/FI2020/050632. (17 pages).

Lee, H. et al., "Biotransformation of dicarboxylic acids from vegetable oil-derived sources: current methods and suggestions for improvement", Applied Microbiology and Biotechnology, 2019, vol. 103, pp. 1545-1555. (11 pages).

Mandelli, D. et al., "Ethenolysis of Esters of Vegetable Oils: Effect of B2O3 Addition To Re2O7/SiO2.Al2O3—SnBu4 and CH3ReO3/SiO2.Al2O3 Metathesis Catalysts", JAOCS, 1996, vol. 76, No. 2, pp. 229-232, AOCS Press. (4 pages).

Metzger, J. O., "Fats and oils as renewable feedstock for chemistry", Eur. J. Lipid Sci. Technol., 2009, vol. 111, pp. 865-876. (13 pages).

Millican, R. C., et al., "The Isolation and Properties of Some Naturally Occurring Octadecenoic (Oleic) Acids", J. Biol. Chem., 1944, vol. 154, pp. 437-450. (15 pages).

Mobley, D. P., "Biosynthesis of Long-Chain Dicarboxylic Acid Monomers From Renewable Resources—Final Technical Report", DE-FC36-95G010099, Apr. 1999 (178 pages).

Mol, J. C., et al., "Metathesis in Oleochemistry", J. Braz. Chem. Soc., 1998, vol. 9, No. 1, pp. 1-11, Soc. Bras. Química. (11 pages).

Spekreijse, J., et al., "The Future of Ethenolysis in Biobased Chemistry", ChemSusChem, 2017, vol. 10, pp. 471-482, Wiley Online Library, Wiley-VCH Verlag Gmbh & Co. KGaA, Weinheim, DE. (13 pages).

Warwel, S., et al., "Polymers and surfactants on the basis of renewable resources", Chemosphere, 2001, vol. 43, pp. 39-48, Elsevier Science Ltd. (10 pages).

Watthanasringkarn, S., et al., "Synthesis of Lubricant from Methyl Ester Palm Stearin", Int'l Journal of Research in Chemical, Metallurgical and Civil Eng., 2015, vol. 2, No. 1, pp. 9-12. (4 pages).

Wheeler, D. H., et al., "The Preparation and Properties of Highly Purified Methyl Oleate", Oil and Soap, Nov. 1939, vol. 16, No. 11, pp. 207-209. (3 pages).

Woo-Young, Jeon, et al.., "Microbial production of sebacic acid from a renewable source: production, purification, and polymerization", Green Chemistry, vol. 21, No. 23, Jan. 2019, pp. 6491-6501. (11 pages).

Wyrębek, P. et al., "Looking for the Noncyclic(amino)(alkyl)carbene Ruthenium Catalyst for Ethenolysis of Ethyl Oleate: Selectivity Is on Target", ACS Omega, Dec. 27, 2018, vol. 3, pp. 18481-18488, ACS Publications. (15 pages).

Churi et al., "A study of metathesis of unsaturated carboxylic esters", Journal of the Oil Technologists Association of India, vol. 25, No. 4, Jan. 1, 1993, pp. 93-95.

Office Action (Notice of First Office Action) issued on Oct. 19, 2022, by the Chinese Patent Office in corresponding Chinese Patent Application No. 202080066686.8, and an English Translation of the Office Action. (19 pages).

Office Action (Notice of First Office Action) issued on Oct. 31, 2022, by the Chinese Patent Office in corresponding Chinese Patent Application No. 202080066719.9, and an English Translation of the Office Action. (17 pages).

Office Action issued on Sep. 16, 2022, by the U.S. Patent and Trademark Office in U.S. Appl. No. 17/762,894. (8 pages).

Office Action issued on Sep. 21, 2022, by the U.S. Patent and Trademark Office in U.S. Appl. No. 17/762,893. (6 pages).

(56) References Cited

OTHER PUBLICATIONS

Office Action issued on Dec. 14, 2022, by the National Intellectual Property Office of China in corresponding Chinese Patent Application No. 202080066687.2, and a machine English translation of the Office Action. (16 pages).

Office Action issued on Feb. 6, 2023, by the U.S. Patent and Trademark Office in U.S. Appl. No. 17/762,893.

RENEWABLE CHEMICAL PRODUCTION ENGAGING METATHESIS AND MICROBIAL OXIDATION

FIELD OF INVENTION

The present process is related to production of diacids via a process combining metathesis and microbial oxidation. Said process utilizes a renewable feedstock comprising glycerides, fatty acid esters or combinations thereof, whereby the diacids produced are renewable as well.

BACKGROUND

Commercial quantities of long-chain diacids are generally not found in nature. Certain long-chain diacids, such as sebacic acid and dodecanedioic acid, have been prepared via chemical methods. For example, starting with benzene or 1,3-butadiene, dodecanedioic acid can be prepared through multiple steps of chemical reactions. One of the best-known process for diacid production is producing pelargonic acid and azelaic acid from oleic acid by ozonolysis. Alternatively, sebacic acid can be prepared through a chemical conversion of castor oil.

A patent application publication, US 2010305354 A1 discloses as an embodiment, a process for producing carboxylic diacids from natural fatty acids or esters by a multistep process comprising two consecutive metathesis reactions, more specifically an ethenolysis and a cross-metathesis. Another document, U.S. Pat. No. 9,023,626 B2, discloses conducting first a microbial oxidation, and then a cross-metathesis to diacids obtained. The first step, microbial oxidation, takes place in aqueous media. Hence, the diacids obtained from fermentation require extensive purification in order to qualify as starting material to metathesis because of sensitivity of the metathesis catalysts. However, the purification sequence of extraction, solvent evaporation, crystallization and recrystallization applied in said process, is incompatible with industrial processes and scale.

Long-chain diacids can also be prepared via biological methods. A biological method, such as fermentation, can produce a series of long-chain diacids containing 9 through 18 carbon atoms. When alkanes are used as substrates, a mixture of monocarboxylic acids and diacids with different chain lengths may be produced. Product distribution is steered by the chain lengths of the feed alkanes and/or due to different metabolic pathways in the microorganism used to perform the fermentation. So far, desired length alkanes have been available as mineral oil derivatives only, and hence, a need for renewable alternatives remains.

For production of long-chain diacids of biological origin, processes use genetically engineered microorganisms at an industrial scale consuming carbon sources other than petroleum derivatives, such as various sugars, fats and oils. The engineered microorganisms are cultured in a suitable liquid medium. The carbon chain typically remains unaltered. Hence, typical oils comprising mainly long-chain fatty acids, produce corresponding renewable long-chain diacids. Since most fatty acids are C16 or C18, high volume production can realistically be considered for C16 or C18 diacids correspondingly.

Fatty acid and/or derivatives thereof used as the Fermentation raw material typically leave traces in the fermentation broth as impurities. Some raw materials also produce a variety of diacid products. Commercial applications of long-chain diacids nevertheless require diacids of very high purity with low quantities of color-inducing impurities and high heat stability. Hence, efficient recovery and separation techniques are needed to separate raw materials and diacids of different chain lengths to yield a product of high purity.

Hence, there is a need for a process for producing renewable carboxylic diacids with improved selectivity towards desired chain lengths. Further, there is a need to recover valuable fractions for refining, and to produce renewable high value products form the remainder of the fractions of the feed material. There is an adjacent need for utilizing the renewable raw material fed to the process as effectively as possible minimizing any waste and lower value use of any side streams. There is still a further need to produce renewable carboxylic diacids. There still is a need to produce carboxylic diacids having carbon numbers, for which production processes so far known in the prior art are not feasible. Further, the present process and production facilities therefor, can be applied for production of carboxylic diacids of different lengths and thereby different characteristics by altering the metathesis reagent, hence the C2-C4 alkene employed.

SUMMARY OF THE INVENTION

Herein is provided a process for producing renewable carboxylic diacids in addition decene from a C6-C22 fatty acid ester containing feedstock, the process comprising:
  a) providing a fatty acid ester containing feedstock, wherein the feedstock contains at least one unsaturated fatty acid ester;
  b) subjecting the feedstock to metathesis reaction conditions in the presence of an alkene selected from C2, C3, C4 alkenes and a metathesis catalyst, to obtain metathesis products comprising renewable alkenes and fatty acid esters;
  c) recovering C10 alkenes comprising 1-decene from the metathesis products;
  d) subjecting a part of the metathesis products after optional pretreatment(s), to microbial oxidation to yield diacids in a fermentation broth;
  e) recovery of the renewable diacids from the fermentation broth.

The process provides a novel route for renewable diacid production. The process is conducted following sequence of steps a, b, c, d, e in said order. The novel combination of metathesis reaction modifying or rearranging carbon skeleton, and producing desired chain lengths, with microbial oxidation into diacids provides several advantages. The process allows efficient use of the feed material. The metathesis provides useful conversion for the unsaturated part of the feed, and the remaining components, when subjected to microbial oxidation, provide further interesting products. Even though the C2-C4 alkene were of fossil origin, the product formed from the present process contains predominantly renewable carbon. The process enables use of renewable raw materials, and in some embodiments even renewable alkene reactants, preferably leading to a totally fossil free process. Further, combination of catalytic and fermentation reactions reduces use of chemicals and organic solvents. The process also provides advantages allowing flexible product options through use of different C2-C4 alkenes in the metathesis reaction.

Embodiments of the present process provide advantages over the prior art. The embodiments also meet some of the needs arising from the prior art, such as producing renewable carboxylic diacids with improved selectivity towards desired chain lengths and carbon numbers. This is achieved by subjecting fatty acid ester containing feedstock to metathesis reaction and fractionating the products thereof prior to microbial oxidation. The renewable hydrocarbons or fatty acids fed to said fermentation are of desired carbon chain lengths producing selectively renewable carboxylic diacids, such as sebacic acid and dodecanedioic acid. The boiling points of diacids are high and distillation poorly suitable for separating diacids form one another. Purification from a mixture of diacids by crystallization is also challenging because of mutual crystallization interferences. Therefore, it is especially advantageous to conduct to the microbial oxidation only the desired carbon chain lengths and obtain a narrower product mix.

The overall process is advantageously designed so that all fractions obtained are further processed creating maximal added value thereto. This is implemented through fractionation and processes where the structures of the carbon chains of each fraction are taken into account and structures existing after metathesis are exploited carefully avoiding where ever possible any need for forming new carbon-carbon bonds and equally avoiding any need for breaking down remaining ones. The present inventors have found that combination of metathesis and microbial oxidation provides an interesting range of valuable renewable products. In addition to most interesting metathesis products, 1-decene and alkyl-9-decenoate, many other products find use on other applications. Such compounds include alkenes, wherein the double bond is not at the alpha-position. Applying microbial oxidation to these compounds provides higher renewable content alternatives to commercial products, but also previously commercially unknown compounds. Microbial oxidation of the metathesis products converts various metathesis reaction products to alpha-omega-dicarboxylic acids, which are particularly interesting for polymerization. Further, since metathesis is known as rearrangement reaction around double bonds within compounds, it is ineffective for saturated fatty acids, such as C16:0 and C18:0, abundant in nature. Microbial oxidation of these saturated fatty acid esters into diacids provides flexible and hydrophobic precursors for manufacturing of polyesters, polyamides and polyurethanes.

BRIEF DESCRIPTION OF DRAWINGS

The process of the current disclosure is depicted by the following figures.

DETAILED DESCRIPTION OF THE INVENTION

Figure 1:
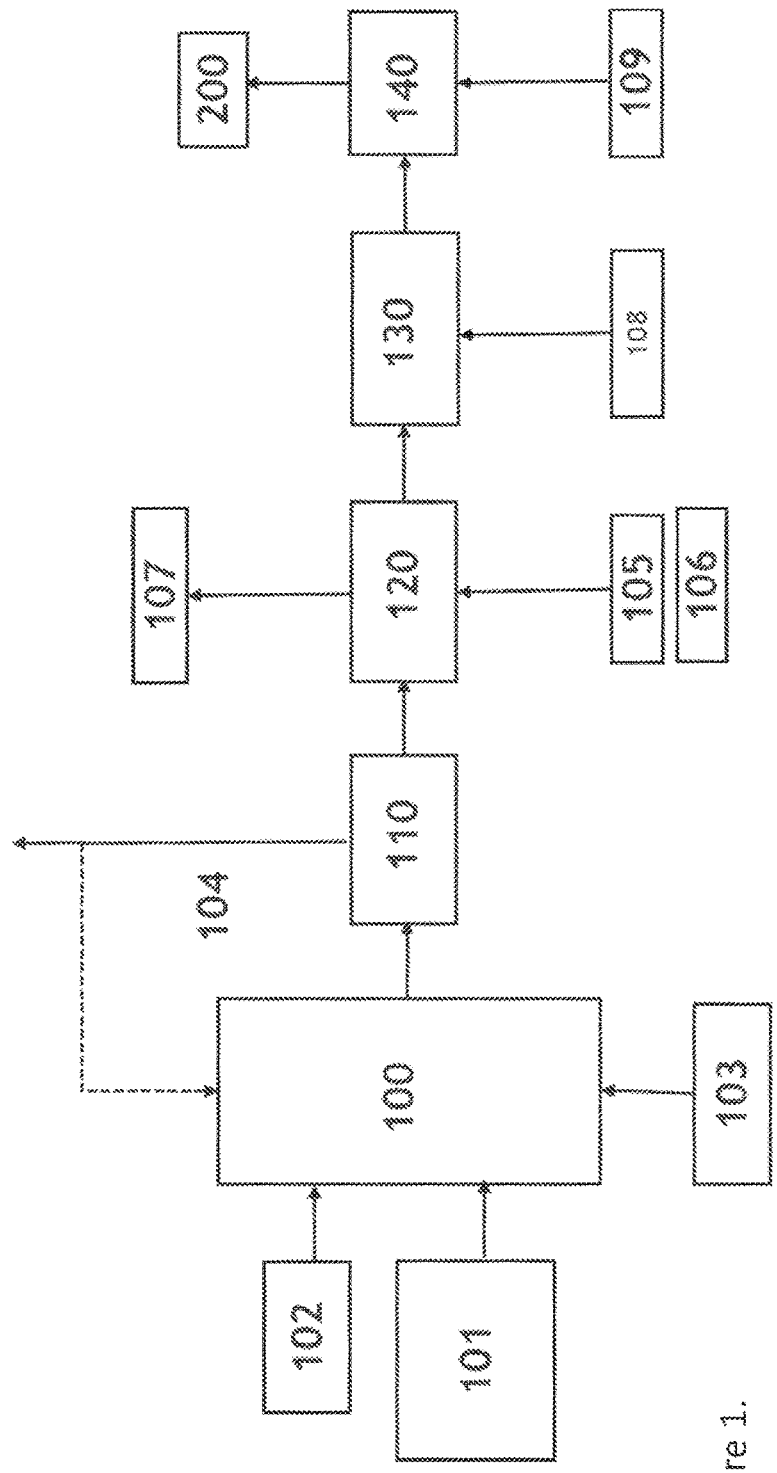
FIG. 1 describes a general process according to the claimed process.

The C6-C22 fatty acid ester containing feedstock as used herein refers to any feedstock comprising esterified fatty acids within the defined carbon chain length. It is essential for the metathesis process that the feedstock contains a compound, in practice compounds, having at least one carbon-carbon double bond.

Typically, the fatty acid ester containing feedstock comprises esterified fatty acids. Oils and fats are typically found in nature as triglycerides, hence of the fatty acid ester containing feedstock is naturally of biological origin. Triglycerides are a common feed containing C6-C22 fatty acids esterified with glycerol. During storage, they may spontaneously degrade to di- and monoglycerides or to free fatty acids, which therefore also appear in feedstocks in industrial processes using natural oils and fats as raw material. For use in the present process, the free fatty acids must be esterified. Particularly suitable feedstocks for the present process are those which comprise C18:1 fatty acid moieties. The feedstock may preferably be characterized as C18 fatty acid ester containing feedstock.

Table 1 lists availability of some C16 and C18 free fatty acids from natural material sources, and the fatty acid carbon chain lengths and unsaturation of exemplary fats and oils found in the literature, possibly suitable for use in the process of the present invention.

TABLE 1

Exemplary C6-C22 fatty acid ester containing feedstocks suitable as feed for the process for producing renewable diacids of the present invention.

| | The fatty acid distribution of glyceride containing feedstocks suitable for the present process (%-wt) | | | | | | | | | | | | | Amount of FFAs [2]Amount of C16 and C18 FFAs |
|---|---|---|---|---|---|---|---|---|---|---|---|---|---|---|
| Fat/oil | 8:0 | 10:0 | 12:0 | 14:0 | 16:0 | 18.0 | 18:1 | 18:2 | 18:3 | 20:0 | 20:1 | 22:0 | 22.1 | |
| Canola | | | | 0.1 | 4.1 | 1.8 | 60.9 | 21.0 | | 0.7 | | 0.3 | | |
| Crude tall oil | | | | | [1]1-2 | | | | | | | | | |
| Cottonseed | | | | 0.7 | 21.6 | 2.6 | 18.6 | 54.4 | 0.7 | 0.3 | | 0.2 | | |
| Crumbe | | | | | 1.7 | 0.8 | 16.1 | 8.2 | 2.9 | 3.3 | | 2.2 | 59.5 | |
| Cuphea (PSR-23) | 0.8 | 81.9 | 3.2 | 4.3 | 3.7 | 0.3 | 3.6 | 2.0 | 0.3 | | | | | |
| Jatropha | | | | | [1]15 | | | | | | | | | 1.5-5 |
| Palm | | | 0.2 | 1.1 | 44.0 | 4.5 | 39.1 | 10.1 | 0.4 | 0.4 | | | | 4-7 |
| Palm Kernel | 3.3 | 3.4 | 48.2 | 16.2 | 8.4 | 2.5 | 15.3 | 2.3 | | 0.1 | 0.1 | | | |
| Palm stearin | | | | | [1]60 | | | | | | | | | 0.1 |
| PFAD | | | | | [1]45 | | | | | | | | | 75-88 |
| Rapeseed | | | | | 2.7 | 1.1 | 14.9 | 10.1 | 5.1 | 10.9 | | 0.7 | 49.8 | |
| Soybean | | | 0.1 | 0.2 | 10.7 | 3.9 | 22.8 | 50.8 | 6.8 | 0.2 | | | | 2.5 |

TABLE 1-continued

Exemplary C6-C22 fatty acid ester containing feedstocks suitable as feed
for the process for producing renewable diacids of the present invention.

| | The fatty acid distribution of glyceride containing feedstocks suitable for the present process (%-wt) | | | | | | | | | | | | | Amount of FFAs [2]Amount of C16 and C18 |
|---|---|---|---|---|---|---|---|---|---|---|---|---|---|---|
| Fat/oil | 8:0 | 10:0 | 12:0 | 14:0 | 16:0 | 18.0 | 18:1 | 18:2 | 18:3 | 20:0 | 20:1 | 22:0 | 22.1 | FFAs |
| Sunflower | | | | | 3.7 | 5.4 | 81.3 | 9.0 | | 0.4 | | | | 0.5 |
| Lard | | 0.1 | 0.1 | 1.5 | 26.0 | 13.5 | 43.9 | 9.5 | 0.4 | 0.2 | 0.7 | | | 5-10 |
| Tallow | | | 0.1 | 3.2 | 23.4 | 18.6 | 42.6 | 2.6 | 0.7 | 0.2 | 0.3 | | | 5-10 |

[1]Values measure at the Analytics lab of Neste Oyj by GC
[2]Estimation of C16-C18 FFAs in %-wt is based on ½ * TAN (total acid number analysis), which is a fair approximation.

According to an embodiment, fatty acid ester containing feedstock comprises fatty acid alkyl esters produced by esterification of glycerides or fatty acids. A widely known and used feed stream is fatty acid alkyl esters, such as fatty acid methyl esters (FAME), produced by a reaction with methanol, either as esterification of fatty acids or as transesterification of glycerides. Another preferred fatty acid alkyl ester is fatty acid ethyl ester (FAEE) obtained from esterification or transesterification with ethanol, preferably bioethanol.

Optional Pretreatment Methods Prior to Metathesis

The fatty acid ester containing feedstock may be pure, but typically contains some impurities that may be harmful for e.g. the metathesis catalyst. Therefore, pretreatment for removal of at least some of these impurities is typically needed or beneficial.

Depending on the feedstock quality, the C6-C22 fatty acid ester containing feedstock to the metathesis reaction may be pretreated if specifically required. These pretreatments include possible removal of water, alcohols and peroxides, preferably to level <10 weight-ppm each.

Alcohols are optionally removed before feeding fatty acid esters to the metathesis reaction. Extraction by water is advantageous for glycerol removal after transesterification. Alcohols, such as methanol and ethanol, when used in excess for esterification, may be removed by distillation. For certain embodiments, a combination of extraction and distillation may be preferred. Preferably the overall process according to the present invention comprises at least one pretreatment step between steps a and b. Such pretreatment step comprises a pretreatment selected from a treatment with an adsorbent, a treatment with a metal alkyl compound, a treatment with a metal alkoxide compound, a treatment with a reducing agent, a treatment with an organic or inorganic drying agent, a thermal treatment or a combination thereof. Preferably the adsorbent is selected from adsorbents able to remove polar components such as water, acids, peroxides or alcohols and/or free radicals (such as decomposition products of peroxides). Preferred metal alkyl compounds comprise trialkyl aluminium compounds, such as triethyl aluminium. Thermal treatment as pretreatment may comprise a thermal treatment, such as evaporation of light polar components or just heating to decompose peroxides.

Some metathesis catalysts are known to be sensitive to impurities. With high catalyst loadings, catalyst poisoning is not immediately observed. However, at the lower limit of catalyst loading, the relative concentration of trace impurities to catalyst becomes larger and activity suffers. One typical class of impurities are organic hydroperoxides, which can be formed in natural oils by oxidative ageing.

The fatty acid alkyl esters may be treated with the magnesium silicate, such as commercially available Magnesol. It has been reported to improve metathesis efficiencies at low catalyst loadings. Another pretreatment option is triethylaluminium treatment alone or together with further compounds, such as $Ac_2O$. Yet another chemical pretreatment method comprises treatment with a metal alkoxides, such as $Al(iPrO)_3$ and $Zr(OEt)_4$.

As physical treatment for peroxide removal heating may be used, such as heating the feedstock to a temperature greater khan 100° C. in the absence of oxygen.

A combination of chemical and physical pretreatments may comprise for example thermal treatment together with an absorbent treatment.

Metathesis

Metathesis is a reaction involving two unsaturated compounds, such as alkenes, each comprising at least one carbon-carbon double bond (C=C). The reaction yields two different unsaturated compounds having undergone a rearrangement.

In the present process, the feedstock is subjected to metathesis reaction conditions in the presence of an alkene selected from C2, C3, C4 alkenes and a metathesis catalyst, to obtain metathesis products comprising renewable alkenes and fatty acid esters.

Metathesis reaction is based on rearrangements around C=C double bonds of two molecules of starting materials. The present application of metathesis aims at producing shorter alkene and ester precursors to microbial oxidation from unsaturated fatty acid esters. This is achieved by reacting unsaturated fatty acid esters with a short chain alkene, such as a C2-C4 alkene to obtain metathesis products comprising renewable alkenes, such as 1-decene, and fatty acid derived esters. Depending on the alkene used, the length of the unsaturated fatty acids and the double bond position therein, a metathesis reaction between these components produces a mixture comprising C5-C14 alkenes and C6-C14 unsaturated esters. Saturated compounds, such as alkyl stearates (C18:0 esters) and alkyl palmitates (C16:0 esters), act as inerts and pass through metathesis reaction unreacted.

As recommended by IUPAC, the term alkene is used here to denote an unsaturated hydrocarbon that contains at least one carbon-carbon double bond. Carbon-carbon double bond, or C=C-bond is also referred to as olefinic bond. In some contexts, such as in reference to poly alpha olefins, olefin is herein used as synonym to alkene.

The metathesis reaction can be catalyzed by one or more metathesis catalysts. Typically, fatty ester metathesis catalysts are homogeneous. In case they could catalyze side reactions in successive reaction steps, it is advantageous to remove them from the solution after metathesis. A non-limiting description of suitable metathesis catalysis include complexes of the type I and II:

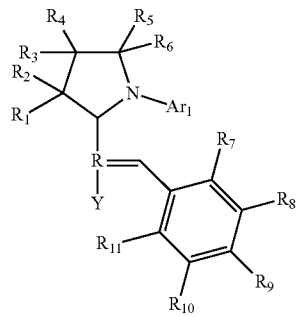

I wherein:
$R_1$-$R_6$=same or different and selected from H, alkyl, cycloalkyl, alkenyl, aryl;
$Ar_1$=phenyl or benzene ring substituted with alkyl, cycloalkyl, alkenyl, Cl, Br, $OR_{12}$ ($R_{12}$=H, alkyl) or an aryl;
$R_7$-$R_{11}$=same or different and selected from H, alkyl, cycloalkyl, alkenyl, aryl, Cl, Br, $NO_2$, $OR_{13}$ ($R_{13}$=H, alkyl), $CH_2NR_{14}R_{15}$ ($R_{14}$, $R_{15}$=alkyl, benzyl, aryl); Y=$NR_{16}R_{17}$ ($R_{16}$, $R_{17}$=alkyl, benzyl, $CH_2$-aryl), $OR_{18}$ ($R_{18}$=alkyl).

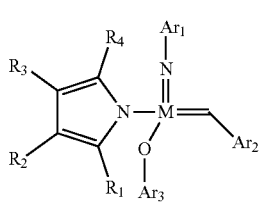

II wherein M=Mo or W;
$R_1$-$R_4$=same or different and selected from H, alkyl, cycloalkyl, alkenyl, aryl, Cl, Br, OR' (R'=H, alkyl);
$Ar_1$, $Ar_2$, $Ar_3$=same or different and selected from phenyl or benzene substituted with alkyl, cycloalkyl, alkenyl, Cl, Br, OR" (R"=H, alkyl) or an aryl.

In prior art, alkylidene complex metathesis catalysis comprising a group 8 transition metal are reported. Said transition metal is preferably selected from ruthenium, molybdenum, osmium, chromium, rhenium, tungsten. Alkene in high purity, typically >99%-vol is fed to metathesis reactor preferably in excess, to avoid self-metathesis of the feed components. Such catalysts are needed in low quantities, for example less than 150 ppm, less than 10 ppm or less than 5 ppm, even from 2 to 4 ppm by weight, as calculated against the fatty acid ester fraction weight fed to metathesis dependent on catalyst complex activity. Catalyst quantity is optimized based on mass transfer to provide continuously more unreacted fatty acid esters or metathesis reagent than metathesis products to the catalyst.

In the present process, metathesis is used for cutting fatty acid structures having carbon numbers typically C18, to molecules having lower carbon numbers with the aid of C2-C4 alkenes, hence shortening of said fatty acid structure. Here, fatty acid structures refer to free fatty acids, fatty acid alkyl esters or mono- di- or triglycerides.

The C2-C4 alkenes are considered here as metathesis reagents and used in excess. The metathesis reagent may be selected from ethene, propene and butenes (1-butene and 2-butene).

Ethene and 2-butene provide advantages through their symmetry resulting in lower product variation. To enable good control of the reactions, typically only one type of alkene at a time is applied. The preferred C2-C4 alkene is ethene. Metathesis with ethene produces alpha olefins and unsaturated fatty acids with the carbon-carbon double bond at terminal position, as metathesis products. Hence, they are particularly useful e.g. as polymerization precursors.

It is considered especially advantageous to use renewable C2-C4 alkene as reagent for metathesis reaction. According to a specific embodiment, this is possible through a combination of a metathesis reaction with a ketonisation reaction releasing renewable alkenes in the same overall process. Accordingly, according to a preferred embodiment, alkenes recovered from a ketonisation reaction of C16 fatty acid ethyl esters are recycled and used in the metathesis reaction.

This can be exemplified with ethene. According to an embodiment, ethene is used as the metathesis reagent, originating from renewable ethanol esterified to fatty acids in esterification or transesterification reaction. In the ketonisation reaction between two fatty acid ethyl esters, such as two C16 fatty acid ethyl esters, renewable ethene originating from said ethanol, is formed. This ethene may be recycled back to the metathesis reaction.

Further, C2-C4 alkene recovered through flash or evaporation after metathesis reaction is preferably recycled back to metathesis reaction.

In embodiments using ethene as reagent, the main reaction taking place is formation of 1-decene and alkyl-9-decenoate, from alkyl oleate and ethene. Side reactions involving further fatty acid esters, such as C18:2 and C18:3, may produce C5-C12 linear alpha olefins (alkenes) and C13-C24 esters. The metathesis reactions are equilibrium reactions and run accordingly. Shorter alkenes form from reactions of polyunsaturated C18:2 and C18:3 fatty acid esters with ethene. An example is given in Scheme 1 illustrating the chain shortening in metathesis reaction.

Scheme 1. Example of metathesis reaction of ethyl oleate and ethene producing 1-decene and ethyl-9-decenoate.

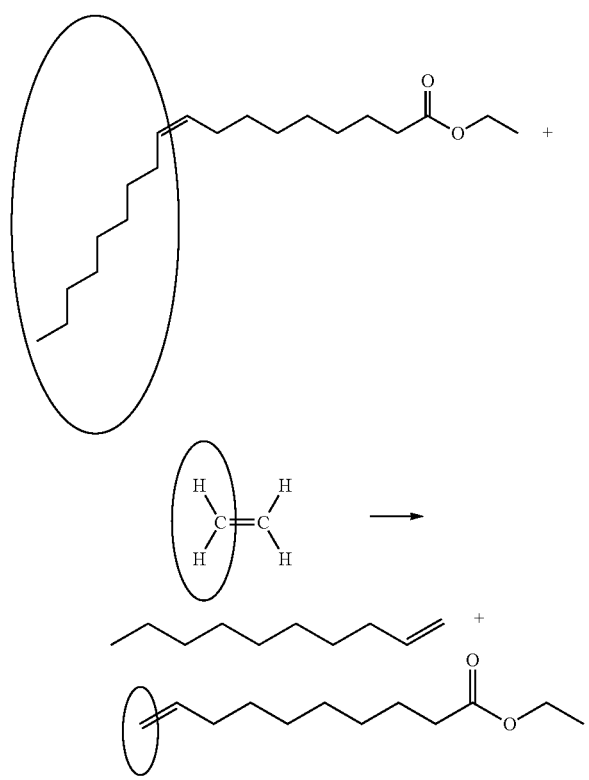

Hence, one interesting embodiment is thus metathesis of unsaturated oleic acid ethyl ester with ethene yielding 1-decene and ethyl-9-decenoate. The ethene required for this reaction may be provided from the subsequent ketonisation reaction of ester feedstock. Advantages gained thereby relate to renewable component production. The unsaturated C18 fatty acid esterified with ethanol produces renewable C10-alkene and ethyl ester of C10 unsaturated fatty acid. Hence, instead of losing part of the original feed into light, such as C1-C4 components, the carbon chain is extended with ethene originating from combined ketonisation reaction fed to the overall process providing more efficient use of the feedstock.

Preferably the metathesis conditions comprise a temperature from 20 to 120° C., more preferably from 20 to 80, most preferably from 30 to 60, a pressure from 0.1 to 3 MPa and a metathesis catalyst, preferably comprising a metal selected from ruthenium, molybdenum, osmium, chromium, rhenium, tungsten, preferably selected from tungsten, ruthenium, molybdenum These conditions are advantageous contributing to solubility of gases and favoring metathesis reactions over side reactions.

The present application of metathesis aims at producing shorter alkenes and esters from unsaturated fatty acids or derivatives thereof, such as esters. This is achieved by reacting the unsaturated fatty acid or derivative thereof with a short chain alkene, such as a C2-C4 alkene. Depending on the length of the unsaturated fatty acids and the double bond position therein, a metathesis reaction between these components produces a mixture comprising C5-C12 alkenes and C6-C14 unsaturated esters.

Metathesis guides the product distribution, especially with regards to the carbon chain length. After microbial oxidation, the most abundant carboxylic diacid obtainable using ethene as metathesis reagent comprise sebacic acid ($C_{10}H_{18}O_4$). Propene or 2-butene as metathesis reagents produce undecanedioic acid ($C_{11}H_{20}O_4$). According to another embodiment, metathesis is conducted using 1-butene as the metathesis reagent alkene. In metathesis reaction with oleic acid ester, it produces dodecane. Subjected to microbial oxidation saturated dodecane produces dodecanedioic acid ($C_{12}H_{22}O_4$).

Separation after Metathesis, such as Alkene Recovery

The process further comprises at least one separation step before subjecting the remaining metathesis products to microbial oxidation in step d). Said separation step may comprise a flash evaporation, distillation, recovery of the metathesis catalyst or a combination thereof.

Metathesis reaction is preferably followed by a flash evaporation step, from which the gaseous lightest alkenes, typically used as metathesis reagents, can be recycled back to metathesis reaction. Removal of said lightest alkenes, contributes to optional following separation steps, such as distillation, which is easier to operate in the absence of lowest boiling components. Hence according to an embodiment the separation in step c) comprises a flash evaporation for removing $C_2$, $C_3$ and $C_4$ alkenes from metathesis products prior to distillation. Such removal stabilizes distillation conditions and provides more efficient recovery of desired fractions. All or some of the $C_2$, $C_3$ and $C_4$ alkenes may be recycled back to metathesis reaction.

As used herein, a "flash evaporation" refers to a rapid release of gaseous components from a stream by pressure control or evaporation. Hence, the C2-C4 alkene recovered through flash evaporation or evaporation after metathesis reaction is preferably recycled back to metathesis reaction.

The process comprises a separation step for recovery of C10 alkenes, comprising 1-decene, before subjecting the remaining metathesis products to microbial oxidation in step d). Said C10 alkenes may be recovered by e.g. distillation. This step recovers a major product dividing the metathesis product stream into portions, the processing of which is feasible. C10 alkenes, especially 1-decene, are attractive products per se and contribute to the overall process economics. A combination of flash evaporation and distillation provides efficient separation.

The overall process for producing 1-decene and renewable carboxylic diacids from a C6-C22 fatty acid ester containing feedstock can be conducted following sequence of steps a, b, c, d, a in said order: a) providing a fatty acid ester containing feedstock, wherein the feedstock contains at least one unsaturated fatty acid ester, b) subjecting the feedstock to metathesis reaction conditions in the presence of an alkene selected from C2, C3, C4 alkenes and a metathesis catalyst, to obtain metathesis products comprising renewable alkenes and fatty acid esters, c) subjecting metathesis products to a separation step to recover C10 alkenes, comprising 1-decene, d) subjecting at least part of the metathesis products after optional pretreatment(s), to microbial oxidation to yield diacids in a fermentation broth, e) recovery of the renewable diacids from the fermentation broth.

As another separation step following the metathesis step, the present process may comprise recovering metathesis catalyst before subjecting the remaining metathesis products to aerobic fermentation. Catalyst removal may improve microbial metabolism and activity.

Hydrolysis

Hydrolysis of fatty acid esters cleaves the esker bond(s) and produces an alcohol and carboxylic acid(s).

According to a preferred embodiment, pretreatment before subjecting the metathesis products to microbial oxidation, comprises hydrolysis of any metathesis products in form of esters. Hydrolysing any esters recovered after metathesis provides then an organic stream comprising fatty acids and alkenes, and an aqueous stream comprising alcohol and water.

Hydrolysis can be carried out catalytically. The aqueous reactions catalyzed by acid, base, or enzymatically, such as by lipase are known in the art. Hydrolysis improves solubility of some fatty acids to the fermentation broth. Base catalyzed hydrolysis may provide further advantages through solubility of salts being even better than that of acids.

The hydrolysis unit comprises equipment materials which are suitable for acidic or corrosive reagents.

After hydrolysis, the stream of fatty acids and alkenes may be fed to the microbial oxidation directly or through further steps. Such steps may comprise fractional distillation or hydrogenation or a combination thereof.

Fractional Distillation

Fractional distillation may be conducted to hydrolyzed metathesis product providing fractions of fatty acids, or to the metathesis product as such, providing fractions of fatty acid alkyl esters corresponding to those described in detail for fatty acids.

According to another embodiment, where the metathesis product is hydrolyzed, the separation after metathesis and hydrolysis (step c) may further comprise fractional distillation and recovery of at least one fraction selected from

- a first fraction comprising at least 80%-wt of the total fraction weight unsaturated fatty acids having a carbon chain length of C10.
- a second fraction comprising at least 80%-wt of the total fraction weight saturated fatty acids having a carbon chain length from C11 to C15;
- a third fatly acid fraction comprising at least 80%-wt of the total fraction weight fatty acids having a carbon chain length C16;
- a fourth fatty acid fraction comprising at least 80%-wt of the total fraction weight fatty acids having a carbon chain length from C17 to C18;
- a fraction comprising renewable alkenes having carbon numbers from C11 to C12.

Advantages relating to fractional distillation comprise better control for product utilization and specific further reactions and steps for each fraction. Renewable chemicals, such as C10:1 alkyl esters, are recoverable, while other fractions may be directed to further processes. In this case at least the second fraction comprising at least 80%-wt of the total fraction weight saturated fatty acids having a carbon chain length from C11 to C15 is subjected to microbial oxidation producing carboxylic diacids of corresponding carbon chain lengths.

With regard to the third fatty acid fraction comprising at least 80%-wt of the total fraction weight fatty acids having a carbon chain length C16, synergy is provided through alkene recycling.

According to a specific embodiment the present process further comprises subjecting the fraction comprising saturated fatty acid esters having carbon chain length of C16, hence palmitates, to ketonisation and hydrotreatment to produce renewable base oil fulfilling the API group III requirements. Herein, unexpected additional synergy has been found when the renewable alkene released during the ketonisation reaction is recycled and used as metathesis reagent.

The alcohol used for esterification, provides in the ketonisation reaction an alkene, that has been found to be usable in the metathesis reaction. Accordingly, the initial feed for the overall process comprises C6-C22 fatty acid ethyl esters, ketonisation releases ethene and the ethene thereby produced is recycled back to metathesis reaction in step b). The same applies to use of C6-C22 fatty acid propyl esters, which yields propene from ketonisation. Propanol may also be renewable, e.g. if produced from glycerol. Preferably single alcohol and corresponding alkene, hence having the same carbon number as the alcohol in esterification, for metathesis are used at a time.

The ketone obtained thereby is further subjected to hydrotreatment, which converts it into paraffin, n- or i-paraffins. The product then meets the API Group III base oil specifications containing ≤0.03 wt-% sulfur, having a viscosity index of ≤120. As to structure, preferably said base oil comprises or consists essentially of C31 paraffins.

Another fraction, the fourth fatty acid fraction comprising at least 80%-wt of the total fraction weight fatty acids having a carbon chain length from C17 to C18, is subjected to hydrotreatment, preferably hydrodeoxygenation and hydroisomerisation, yielding at least one component selected from renewable diesel, renewable naphtha, renewable aviation fuel, and renewable gasoline.

A fraction comprising renewable alkenes having carbon numbers from C11 to C12 (beta or gamma olefins) may be obtainable by using propene or butenes as metathesis reagent. Preferably they are hydrogenated prior to microbial oxidation to corresponding renewable alkanes.

Hydrogenation

According to some embodiments, both the alkenes and unsaturated fatty acids recovered from hydrolysis are next subjected to hydrogenation reaction. The pretreatment of the present process comprises the hydrogenation of the metathesis products in the form of alkenes and unsaturated fatty acids before subjecting said metathesis products to microbial oxidation. Hydrogenation saturates carbon-carbon double bonds and yields alkanes and saturated fatty acids before the fermentation.

According to one embodiment of the present process, the hydrogenation of renewable alkenes to saturate any C=C double bonds in the step d) is carried out before the microbial oxidation of hydrogenated product. Hence, the hydrocarbons fed to the microbial oxidation are alkanes, saturated fatty acids or a combination thereof. By using alkanes, the oxidation reactions take place within the terminal carbons and interference of C=C double bonds to oxidation reactions can be avoided.

Some micro-organisms produce enzymes with such selectivity that oxidation only takes place in the terminal carbons and leave C=C double bonds unreacted. Then they may be saturated only after fermentation and recovery from fermentation broth. According to this embodiment, the renewable diacids recovered from the fermentation broth may be subjected to hydrogenation to saturate any C=C double bonds, hence the reaction taking place after microbial oxidation. This embodiment provides advantages when the feed to the fermentation comprises unsaturated fatty acids recovered after metathesis and fractionating distillation in addition to recovered renewable alkenes. Unsaturated fatty acids show better solubility and less hydrophobicity in aqueous environment, which improves reaction rate and efficiency in fermentation.

Microbial Oxidation/Fermentation

The step of fermentation as disclosed herein utilizes genetically engineered microorganisms to produce carboxylic diacids at an industrial scale using carbon sources other than petroleum such as renewable alkenes, alkanes or fatty acids of desired length. The engineered microorganisms can be cultured in a suitable liquid medium containing a carbon source as well as other required nutrients. When cultured under desirable temperature, pH, dissolved oxygen and the like, the microorganisms can produce and secrete the carboxylic diacids into the culture medium also referred to as fermentation broth. The carboxylic diacids can then be separated from this fermentation broth and purified to the extent necessary for use in particular industrial processes.

As used herein, the term "fermentation broth" refers to the broth obtained after completion of fermentation and/or bioconversion by a microorganism in a cultivation medium which includes a nitrogen source, at least one organic substrate, and optionally a co-substrate.

The present invention comprises several embodiments, wherein the park of the metathesis products subjected to microbial oxidation varies.

The substrates to microbial oxidation may comprise fatty acid esters, fatty acids, fatty acid salts, alkenes, alkanes or combinations thereof obtained from the metathesis reaction and optionally treated by hydrolysis, hydrogenation or a combination thereof prior to fermentation. Different substrates have varying solubilities to the cultivation medium, which should be taken into account in process design. For example, in case the acid is solid but an ester thereof liquid at the fermentation temperature, it is preferable to feed said substrate to fermentation in acid form and not perform hydrolysis.

According to an embodiment illustrated in FIG. 1, the metathesis product is subjected to olefin flash evaporation for recycle of metathesis reagents, after which the stream comprising all fatty acid esters and alkenes are directed to next steps. The stream also comprises saturated fatty acid esters flowing through metathesis as inerts (wherein most abundant are C16:0 esters), hence ending up to the product stream. Before microbial oxidation, said stream is subjected to hydrolysis and hydrogenation yielding saturated fatty acids and alkanes. The microbial oxidation according to this embodiment produces renewable carboxylic diacids with high variety of lengths.

Figure 2:
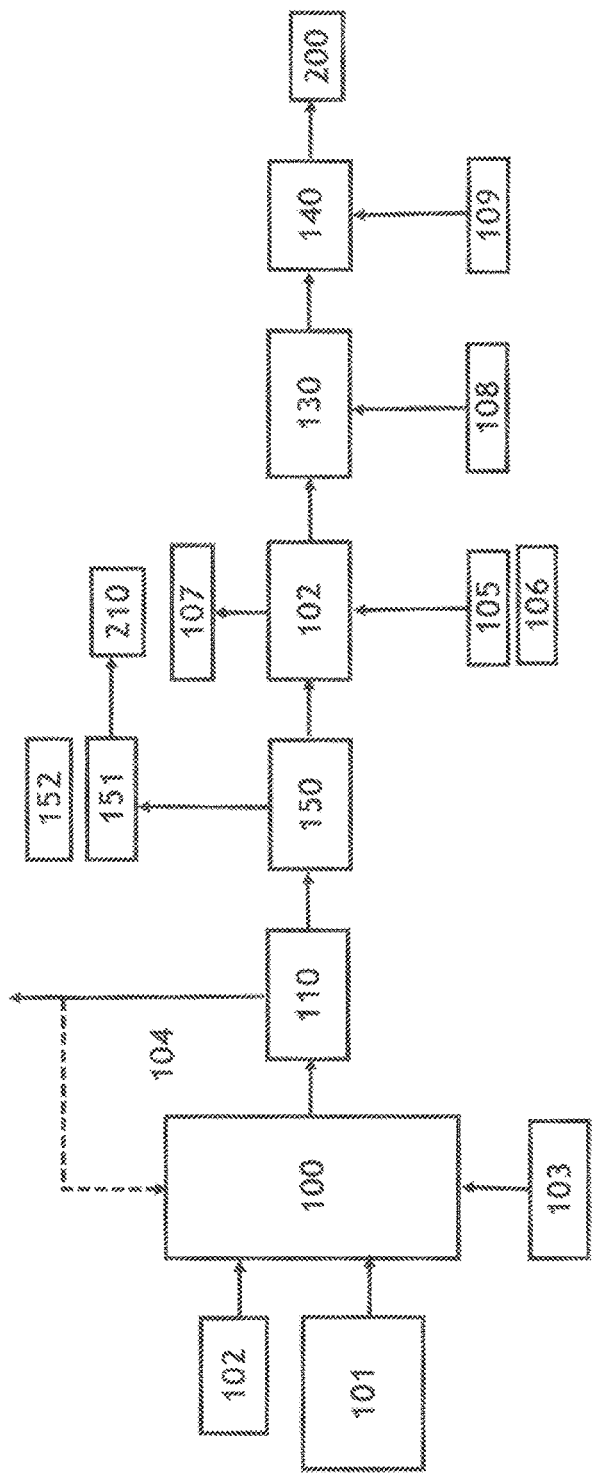
FIG. 2 illustrates schematically another embodiment of the present invention, wherein C5-C10 alkenes are separated from the metathesis product stream, and the rest of the metathesis product is directed to the microbial oxidation.

According to an embodiment illustrated in FIG. 2, the metathesis product is again subjected to olefin flash evaporation for recycle of metathesis reagents. Then only C10 alkenes, 1-decene therein, are removed from the metathesis products and remaining metathesis product fractions comprising fatty acid esters and alkenes other than C10, are directed to next steps. The stream also comprises saturated fatty acid esters flowing through metathesis as inerts, hence ending up the product stream. Before microbial oxidation, said stream is subjected to hydrolysis and hydrogenation yielding saturated fatty acids and alkanes. The microbial oxidation according to this embodiment produces renewable carboxylic diacids with high variety of lengths.

Figure 3:
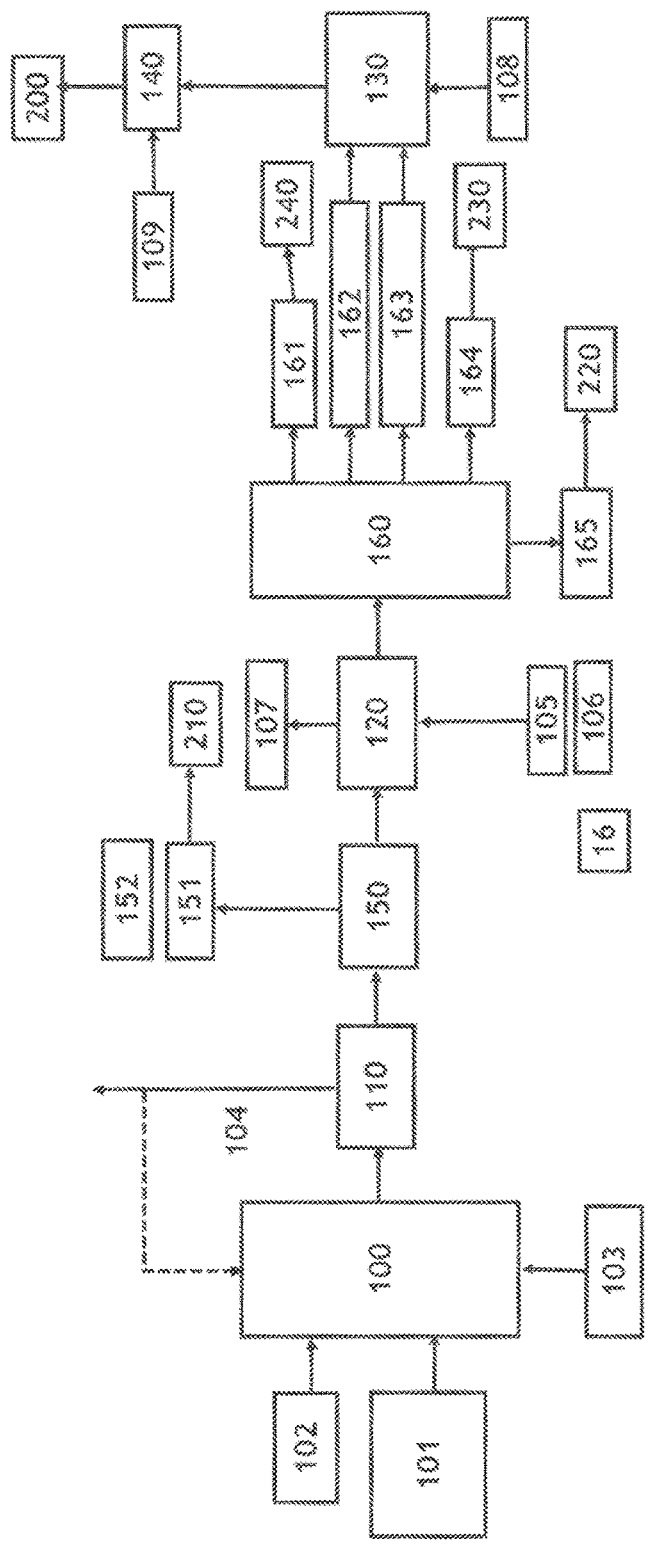
FIG. 3 illustrates schematically yet another embodiment of the present invention, wherein the fraction fed to microbial oxidation is relatively limited.

According to an embodiment illustrated in FIG. 3, the metathesis product is again subjected to olefin flash evaporation for recycle of metathesis reagents. Then C5-C10 alkenes are removed by distillation from the metathesis products and remaining metathesis product fractions comprising fatty acid esters and C11-C12 alkenes are directed to next steps. The stream also comprises saturated fatty acid esters flowing through metathesis as inerts, such as palmitates, ending up to the product stream. Said stream is subjected to hydrolysis yielding a mixture of fatty acids and alkenes, which is subjected to another distillation, from which only fractions comprising C11-C12 alkenes and C11-C15 fatty acids are subjected to hydrogenation and microbial oxidation. Other fractions are recovered and subjected to further refining. Hence, the process according to this embodiment produces renewable carboxylic diacids with carbon numbers from C11 to C15.

According to a specific embodiment, the hydrocarbons fed to the fermentation are not hydrotreated beforehand. Microbial oxidation is selective to terminus of the molecule only and carbon-carbon double bond does not interfere with oxidation. If desired, unsaturated diacids may be isolated by solvent extraction from fermentation broth and hydrogenated catalytically alter recovery. Another option for recovered unsaturated carboxylic diacids is further reaction with an oxidizing agent to oxidatively cleave the carbon-carbon double bonds to carboxyl groups to form polycarboxylic acids.

Fermentation produces a concentrated broth, such as fermenting *C. tropicalis* strain H5343 (ATCC 20962). Fermentation of oleic acid with strain 145343 under standard fermentation conditions may produce a broth comprising 100-140 g/l dicarboxylic acids which corresponds to 10-14 weight % dicarboxylic acids based on the total weight of the feed.

A microorganism used for microbial oxidation is typically suitable for genetic manipulation and often can be cultured at cell densities useful for industrial production of a target fatty dicarboxylic acid product.

A host microorganism sometimes is a native microorganism, and at times is a microorganism that has been engineered. Strains capable of oxidizing only terminal methyl into acids through genetic engineering are available. Hence, such strains provide solely alpha-oxidation at both termini of the substrate molecule, which can also be referred as alpha-omega-oxidation.

In some embodiments an engineered microorganism is a single cell organism, often capable of dividing and proliferating. A microorganism can include one or more of the following features: aerobe, anaerobe, filamentous, non-filamentous, monoploid, diploid, auxotrophic and/or non-auxotrophic. In certain embodiments, an engineered microorganism is a prokaryotic microorganism (e.g., bacterium), and in certain embodiments, an engineered microorganism is a non-prokaryotic microorganism. In some embodiments, an engineered microorganism is a eukaryotic microorganism (e.g., yeast, fungi, amoeba). In some embodiments, an engineered microorganism is a fungus. In some embodiments, an engineered organism is a yeast.

Suitable yeast for fermentation according to the present process may be selected from those discussed in paragraph [0058] of US2016298145A1. Preferred yeast may be selected of the genus *Candida* yeasts, such as *C. revkauli, C. viswanathii, C. pulcherrima, C. tropicalis, C. utilis*, more preferably among genetically modified *Candida tropicalis* strains. Said genetical modification may include beta-oxidation blocking. Any suitable strains from *Candida* spp. yeast may be utilized as parental strains for genetic modification.

Preferably, the microorganism is a partially or completely beta-oxidation blocked.

As the last step f, the renewable diacids are recovered from the fermentation broth. Several techniques for separating carboxylic acids from the various impurities present in the fermentation broth are known. Typically, cells need to be removed first from the aqueous portion of the fermentation broth using various techniques such as filtration and centrifugation. Many methods for following product recovery are based on selectively permeable membranes.

According to one embodiment, the fermentation broth is first separated into aqueous phase and oily phase, which oily phase is recovered from the top of the tank, repeatedly if needed. The cells and nutrients remain in the aqueous phase, while products can be recovered from the oily phase. Desired diacid may be separated from impurities by crystallization and appropriate heating/cooling sequences thereto.

Carboxylic diacids may also be separated from other impurities in the fermentation broth by techniques involving separation of the biomass from the fermentation broth, precipitation of the carboxylic acid from the fermentation broth, and recovery of the crystals from the broth. For separation of long chain dicarboxylic acids from a fermentation broth it has also been suggested to add diatomaceous earth to the fermentation broth, filtering the broth under pressure, and then precipitating the dicarboxylic acid from the broth using a mineral acid and heating.

Another approach includes separating the biomass from the fermentation broth, heating the cell-free broth at a pH above 7.0, regulating the pH to below 3.0 using an inorganic acid, and recovering the dicarboxylic acid crystals. Further methods involving heat and pH-adjustment treatments are known in the field.

The carboxylic diacid of interest can be purified by reducing the pH al the aqueous medium, exposing the carboxylic diacid of interest to at least one suitable organic solvent, and optionally altering the temperature of the mixture of the at least one suitable organic solvent and carboxylic diacid of interest. In some embodiments, additional processing steps such as centrifugation or filtration can be selectively employed to further purify the carboxylic diacid of interest.

According to an embodiment, it is possible to perform the purification of diacids without organic solvents. Advantages related to such embodiment include elimination of a need for recovery of the solvents and prevention of hazardous emissions thereof. This purification method achieves very high purities al dicarboxylic acids as a final product, e. g., 96.0% or higher based on the total weight of the product and has proven efficient even when impurities that are present in the feed, such as monocarboxylic acids, have properties which are very similar to desired dicarboxylic acids.

According to one embodiment, the separation and purification of at least one long-chain diacid may be conducted by means of chromatography.

As one aspect, herein is provided use of a metathesis reaction of fatty acid esters combined with a microbial oxidation for producing renewable carboxylic diacids. Preferably, this use is combined with refining the other streams available, such as the one comprising renewable base oil production as described in detail above. More preferably, the use further comprises renewable fuel production.

Products

As used herein, dicarboxylic acids and carboxylic diacids, fatty dicarboxylic acids and sometimes diacids, are used as synonyms and refer to compounds having two —COOH— groups. They refer to fatty acid derivatives having COOH-group at both ends of the linear carbon chain. Many microbial strains of interest herein have an intrinsic tendency for β-oxidation. As β-oxidation is undesirable the microbial strains used may be β-oxidation blocked (β-blocked or beta-blocked) by means of genetic engineering. Preferably dicarboxylic acids formed in the method according to present invention are alpha-omega dicarboxylic acids (or αω-dicarboxylic acids), in which said two acid moieties are found at each terminus of a linear molecule. The preferred renewable αω-carboxylic diacids produced herein comprise decanedioic acid ($C_{10}H_{18}O_4$), undecanedioic acid ($C_{11}H_{20}O_4$) and dodecanedioic acid ($C_{12}H_{22}O_4$).

The reference "renewable" in relation to the products obtainable from the present process, refers to high renewable carbon content in the products. Typically, renewable carbon predominates that of fossil origin. In specific cases, all carbon of a product may be of renewable origin. However, it is generally accepted that some reagents, such as hydrogen, used in the processes may originate from non-renewable sources and yet the product is considered renewable. The renewable content may be determined from both the starting materials and the products, by isotopic distribution involving $^{14}C$, $^{13}C$ and/or $^{12}C$ as described in ASTM D6866. According to the present disclosure the renewable products obtained, such as diacids, have a $^{14}C$ concentration of the total carbon content that is clearly measurable and distinct from that of fossil products, preferably more than 50 wt-%, more preferably more than 90 wt-%, most preferably more than 98 wt-%, such as 99 wt-% or higher.

Embodiments described herein provide renewable diacids with carbon numbers from C11 to C15. Such diacids are attractive linear precursors to polymerization, which otherwise are not readily available commercially. Within polymers, the carbon chain length can be utilized for steering end product characteristics, such as brittleness, elasticity, melting point. Hence, such polymer precursors may even enable design and production of novel polymer materials.

Diacids obtainable from various embodiments provide advantages. Embodiments, where saturated esters, such as palmitates (C16:0 esters) and stearates (C18:0 esters), flow through metathesis and are eventually fed to microbial oxidation as corresponding acids, provide very interesting C16 and C18 diacids correspondingly. Compared to palmitic and stearic acids as such, C16 and C18 diacids provide flexible and hydrophobic precursors for manufacturing of polyesters, polyamides and polyurethanes.

Provided herein are methods for producing a fatty dicarboxylic acid (also referred to herein as a diacid). Any suitable diacid can be produced, and a diacid produced often includes acid moieties at each terminus of the molecule (e.g., alpha omega diacids). A diacid sometimes is a C4 to a C24 diacid (i.e., a diacid containing 4 carbons to 24 carbons) and sometimes is a C8, C10, C12, C14, C16, C18, or C20 diacid. Yeast and processes herein are capable of producing a diacid containing an odd number of carbons, and sometimes a product contains one or more diacids chosen from a C5, C7, C9, C11, C13, C15, C17, C19, C21 and C23 diacid. A hydrocarbon portion of a diacid sometimes is fully saturated and sometimes a diacid includes one or more unsaturations (e.g., double bonds).

Specifically interesting carboxylic diacids comprise octanedioic acid, decanedioic acid, dodecanedioic acid, tetradecanedioic acid, hexadecanedioic acid, octadecanedioic acid, eicosanedioic acid.

Exemplary products in relation to specific embodiments of the present invention are listed in tables 2 and 3.

TABLE 2

Exemplary products obtainable from embodiments of the present invention applying various sequences of the process steps.

| Process | FAME feedstock | FAME main components | Olefin | after metathesis | distilled out after metathesis | after hydrolysis | after hydrogenation | after fermentation |
|---|---|---|---|---|---|---|---|---|
| An embodiment according to FIG. 1 | palm | C16:0 ME C18:1 ME C18:2 ME | ethene | C10:1 ME C13:2 ME C16:0 ME 1-decene 1,4-decadiene 1-heptene | | acid C10:1 acid C13:2 acid C16:0 1-decene 1,4-decadiene 1-heptene | acid C10:0 acid C13:0 acid C16:0 decane heptane | sebacic acid (C10) tridecanedioic acid (C13) hexadecanedioic acid (C16) pimelic acid (C7) |
| An embodiment according to FIG. 1, no hydrogenation | palm | C16:0 ME C18:1 ME C18:2 ME | ethene | C10:1 ME C13:2 ME C16:0 ME 1-decene 1,4-decadiene 1-heptene | | acid C10:1 acid C13:2 acid C16:0 1-decene 1,4-decadiene 1-heptene | | acid C10:1 acid C13:2 hexadecanedioic acid (C16) acid C10:2 acid C7:1 |
| An embodiment according to FIG. 2 | palm | C16:0 ME C18:1 ME C18:2 ME | ethene | C10:1 ME C13:2 ME C16:0 ME 1-decene 1,4-decadiene 1-heptene | 1-decene 1,4-decadiene 1-heptene 1,4-pentadiene | acid C10:1 acid C13:2 acid C16:0 | acid C10:0 acid C13:0 acid C16:0 | sebacic acid (C10) tridecanedioic acid (C13) hexadecanedioic acid (C16) |

TABLE 3

Exemplary products obtainable from embodiments of the present invention applying various sequences of the process steps according to FIG. 3, where hydrolysis is applied and distillations applied after both metathesis and hydrolysis.

| FAME feedstock | FAME main components | Olefin | after metathesis | distilled out after metathesis | after hydrolysis | distilled out before hydrogenation | after hydrogenation | after fermentation |
|---|---|---|---|---|---|---|---|---|
| palm | C16:0 ME C18:1 ME C18:2 ME | ethene | C10:1 ME C13:2 ME C16:0 ME 1-decene 1,4-decadiene 1-heptene | 1-decene 1,4-decadiene 1-heptene | acid C10:1 acid C13:2 acid C16:0 | acid C10:1 acid C16:0 | acid C13:0 | tridecanedioic acid (C13) |
| palm | C16:0 ME C18:1 ME C18:2 ME | 1-butene | C10:1 ME C12:1 ME C13:2 ME C15:2 ME C16:0 ME 1-decene 3-dodecene 1,4-decadiene 3,5-dodecadiene 1-heptene 3-nonene | 1-decene 1,4-decadiene 1-heptene 3-nonene | acid C10:1 acid C12:1 acid C13:2 acid C15:2 acid C16:0 3-dodecene 3,5-dodecadiene | acid C10:1 acid C16:0 | acid C12:0 acid C13:0 acid C15:0 dodecane | dodecanedioic acid (C15) tridecanedioic acid (C15) pentadecanedioic acid (C15) |
| rapeseed | C18:1 ME C18:2 ME C18:3 ME | ethene | C10:1 ME C13:2 ME C16:3 ME 1-decene 1,4-decadiene 1,4,7-decatriene 1-heptene 1,4-heptadiene | 1-decene 1,4-decadiene 1,4,7-decatriene 1-heptene | acid C10:1 acid C13:2 acid C16:3 | acid C10:1 acid C16:3 | acid C13:0 | tridecanedioic acid (C13) |

Regarding the desired products, esterified palm oil or palm oil fatty acids provide especially advantageous feed. PFAD is especially rich in oleic acid. Metathesis reaction between oleic acid ethyl ester and ethene produces 1-decene and ethyl-9-decenoate. Of these, 1-decene is especially attractive as a component for poly alpha olefin (PAO) production which again may be used for lubricant manufacture. Among other unsaturated C10-C15 fatty acid esters, ethyl-9-decenoate is interesting for refining into oleo chemicals. Other preferable feedstocks comprise rape seed oil and soya oil yielding homogenous product range. Most preferred feeds are obtained from high oleic sunflower oils, wherein the proportion of unsaturated fatty acid esters (C18:1,2,3) is high 85-90% (GMO).

The invention is next discussed with reference to attached figures.

FIG. 1 illustrates schematically an embodiment of the present invention, wherein the metathesis product is directed to the microbial oxidation in its' entirety after C10 alkene recovery (not shown). As feed, purified C16-C22 fatty acid methyl esters 102 and a C2-C4 alkene 101 are fed to metathesis reaction 100. Some of said C16-C22 fatty acid methyl esters (FAME) are unsaturated. A metathesis catalyst 103 is also fed to the metathesis reaction 100. The product therefrom comprises alkenes and fatty acids formed during metathesis reaction, but also saturated FAME, which flows through metathesis reaction 100 as unreacted. Said product is subjected to olefin flash 110, which releases gaseous compounds, such as C2-C4 alkenes, which are recycled 104 back to metathesis reaction 100. The gas depleted metathesis product is next fed to hydrolysis 120, with water 105 and catalyst 106. Hydrolysis cleaves ester bonds releasing methanol 107 from methyl esters yielding fatty acids. Alkenes, which did not react in hydrolysis saturate in hydrogenation 130 in the presence of hydrogen 108 into alkanes. The mixture of fatty acids and alkanes is fed to microbial oxidation 140, where aerobic fermentation to yields diacids in a fermentation broth. The terminal methyl of fatty acids and both termini of alkanes are oxidized to carboxyl groups. Renewable diacids 200 are recovered from the fermentation broth.

FIG. 2 illustrates schematically another embodiment of the present invention, wherein C5-C10 alkenes are separated from the metathesis product stream, and the rest of the metathesis product is directed to the microbial oxidation. Again, the feed is purified C16-C22 fatty acid methyl esters 102. An C2-C4 alkene 101 and a metathesis catalyst 103 are also fed to the metathesis reaction 100. Some of said C16-C22 fatty acid methyl esters (FAME) are unsaturated. The product therefrom comprises alkenes and fatty acids formed during metathesis reaction, but also saturated FAME, which flows through metathesis reaction 100 as unreacted. Said product is subjected to olefin flash 110, releasing gaseous compounds recycled 104 back to metathesis reaction 100. The gas depleted metathesis product is next subjected to alkene distillation, recovering C5-C10 alkenes 151 and 152, wherefrom C10 olefins, comprising 1-decene can be recovered as product 151. Said 1-decene 151 is usable as precursor to renewable poly-alpha-olefin 210 production. The C2-C10 alkene depleted metathesis product is next fed to hydrolysis 120, with water 105 and hydrolysis catalyst 106. Hydrolysis cleaves ester bonds releasing methanol 107 from methyl esters yielding fatty acids. Remaining alkenes, in practice C11-C12 alkenes, which did not react in hydrolysis, are next saturated in hydrogenation 130 in the presence of hydrogen 108 into C11-C12 alkanes. Hydrogenation serves also the unsaturated fatty acids, which are then saturated. The mixture of saturated fatty acids and alkanes is fed to microbial oxidation 140, where aerobic fermentation yields diacids in a fermentation broth. The terminal methyl of fatty acids and both termini of alkanes are oxidized to carboxyl groups. Renewable diacids 200 are recovered from the fermentation broth.

FIG. 3 illustrates schematically yet another embodiment of the present invention, wherein the fraction fed to microbial oxidation is relatively limited. The feed is purified C16-C22 fatty acid methyl esters 102 and fed to metathesis reaction 100. An C2-C4 alkene 101 and a metathesis catalyst 103 are also fed to the metathesis reaction 100. Some of said C16-C22fatty acid methyl esters (FAME) are unsaturated. The product therefrom comprises alkenes and fatty acids formed during metathesis reaction, but also saturated FAME, which flows through metathesis reaction 100 as unreacted. Said product is subjected to olefin flash 110, releasing gaseous compounds recycled 104 back to metathesis reaction 100. The gas depleted metathesis product is next subjected to alkene distillation, recovering C5-C10 alkenes 151 and 152, wherefrom C10 alkenes, comprising 1-decene can be recovered as product 151. Said 1-decene 151 is usable as precursor to renewable poly-alpha-olefin 210 production. The C2-C10 alkene depleted metathesis product is next fed to hydrolysis 120, with water 105 and hydrolysis catalyst 106. Hydrolysis cleaves ester bonds releasing methanol 107 from methyl esters yielding fatty acids. The hydrolysis product, hence fatty acids and C11-C12 alkenes are next subjected to distillation 160. The distillation 160 divides the stream into several fractions and optionally can be conducted without hydrolysis, yielding fractions of corresponding fatty acid esters and alkenes. Lightest unsaturated C10:1 fatty acids 161 are recovered and usable as polymer chemicals 240. The remaining alkenes, C11 and C12 alkenes 162, which did not react in hydrolysis, are next saturated in hydrogenation 130 together with C11-C15 fatty acids, which after hydrogenation in the presence of hydrogen 108 are all saturated. The mixture of saturated fatty acids and alkanes is fed to microbial oxidation 140, where microbial oxidation with air feed 109 yields diacids in a fermentation broth. Renewable diacids 200 are recovered from the fermentation broth.

In one embodiment according to FIG. 2 1-decene, dodecane diacids, such as DDDA (dodecanedioic acid) and/or sebacic acid are produced via combined metathesis and microbial oxidation route.

The invention claimed is:

1. A process for producing 1-decene and renewable carboxylic diacids from a C6-C22 fatty acid ester containing feedstock, the process comprising:
   a) providing the C6-C22 fatty acid ester containing feedstock, wherein the feedstock contains at least one unsaturated fatty acid ester;
   b) subjecting the feedstock to metathesis reaction conditions in a presence of (1) an alkene selected from the group consisting of a C2 alkene, a C3 alkene, a C4 alkene and a combination thereof, and (2) a metathesis catalyst, to obtain metathesis products containing renewable alkenes and fatty acid esters;
   c) recovering C10 alkenes, containing 1-decene from the metathesis products;
   d) subjecting a part of the metathesis products including the fatty acid esters to a pretreatment, wherein the pretreatment includes producing fatty acids from the fatty acid esters, and subjecting the fatty acids to microbial oxidation in a presence of genetically engineered microorganisms cultured in a liquid medium containing a carbon source and other nutrients, to yield a plurality of renewable diacids each having a carbon number from C10 to C15 in a fermentation broth; and e) recovering the plurality of renewable diacids from the fermentation broth.

2. The process according to claim 1, wherein the pretreatment in step d) which includes hydrolysis of the fatty acid esters of the metathesis products before conducting the microbial oxidation in step d).

3. The process according to claim 1, wherein the pretreatment in step d) includes hydrogenation of the alkenes of the metathesis products and optionally unsaturated fatty acids before conducting the microbial oxidation in step d).

4. The process according to claim 1, comprising:
subjecting renewable diacids recovered from the fermentation broth to hydrogenation to saturate any C=C double bonds.

5. The process according to claim 1, comprising:
subjecting the fatty acid ester containing feedstock from step a) to a pretreatment selected from at least one or more of a treatment with an adsorbent, a treatment with a metal alkyl compound, a treatment with a metal alkoxide compound, a treatment with a reducing agent, a treatment with an organic or inorganic drying agent, a thermal treatment and/or a combination thereof.

6. The process according to claim 1, further comprising recovering a metathesis catalyst before conducting the microbial oxidation in step d).

7. The process according to claim 1, wherein separation in step c) comprises:
a flash evaporation for removing a gaseous fraction.

8. The process according to claim 1, wherein the alkene used in the metathesis reaction is ethene, 2-butene, or a combination thereof.

9. The process according to claim 1, wherein the alkene used in the metathesis reaction is propene or 1-butene.

10. The process according to claim 1, wherein metathesis conditions comprise:
a temperature from 20 to 120° C., a pressure from 0.1 to 3 MPa and a metathesis catalyst containing a metal selected from the group consisting of ruthenium, molybdenum, osmium, chromium, rhenium, and tungsten.

11. The process according to claim 2, wherein step d) further comprises:
fractional distillation and recovery of at least one fraction selected from at least one or more of:
a first fraction containing at least 80%-wt of the total fraction weight unsaturated fatty acids having a carbon chain length of C10;
a second fraction containing at least 80%-wt of the total fraction weight saturated fatty acids having a carbon chain length from C11 to C15;
a third fatty acid fraction containing at least 80%-wt of the total fraction weight fatty acids having a carbon chain length C16;
a fourth fatty acid fraction containing at least 80%-wt of the total fraction weight fatty acids having a carbon chain length from C17 to C18; and/or
a fraction containing renewable alkenes having carbon numbers from C11 to C12.

12. The process according to claim 11, comprising:
subjecting the third fatty acid fraction containing fatty acids having a carbon chain length C16, to ketonisation and hydrotreatment to produce renewable base oil fulfilling API group III requirements.

13. The process according to claim 11, comprising:
subjecting the third fatty acid fraction containing fatty acids having a carbon chain length C16, to ketonisation whereby ethene is released, recovered and recycled back to metathesis reaction in step b).

14. The process according to claim 11, comprising:
subjecting the fourth fatty acid fraction to hydrotreatment, whereby at least one component is obtained selected from renewable diesel, renewable naphtha, renewable aviation fuel, and renewable gasoline.

15. The process according to claim 1, wherein separation in step c) comprises:
a flash evaporation for removing a gaseous fraction containing $C_2$ to $C_4$ alkenes from the metathesis products, and recycling them back to the metathesis reaction.

16. The process according to claim 2, wherein the pretreatment in step d) includes hydrogenation of the alkenes of the metathesis products and optionally unsaturated fatty acids before conducting the microbial oxidation in step d).

17. The process according to claim 2, comprising:
subjecting the plurality of renewable diacids recovered from the fermentation broth to hydrogenation to saturate any C=C double bonds.

18. The process according to claim 1, wherein the plurality of renewable diacids each having a carbon number from C10 to C15 are saturated.

19. The process according to claim 1, wherein the plurality of renewable diacids each having a carbon number from C10 to C15 are unsaturated.

20. The process according to claim 1, wherein the plurality of renewable diacids each having a carbon number from C10 to C15 comprises at least one selected from the group consisting of decanedioic acid, undecanedioic acid, dodecanedioic acid, tridecanedioic acid, tetradecanedioic acid, and pentadecanedioic acid.

21. The process according to claim 1, wherein the plurality of renewable diacids each having a carbon number from C10 to C15 comprises at least one selected from the group consisting of a C11 diacid, a C13 diacid, a C15 diacid, and a combination thereof.

22. The process according to claim 1, wherein the step of subjecting the fatty acids to microbial oxidation does not include subjecting a hydrocarbon to microbial oxidation.

23. The process according to claim 1, wherein the feedstock contains a C18 fatty acid ester.

* * * * *